United States Patent [19]

Hamma et al.

[11] 4,043,991

[45] Aug. 23, 1977

[54] PREPARATION OF PEPTIDES AND CEPHALOSPORINS

[75] Inventors: Noritaka Hamma, Sakai; Masataka Fukumura, Kobe; Kaoru Maeshima, Takarazuka; Takenari Nakagome, Nishinomiya, all of Japan

[73] Assignee: Sumitomo Chemical Company, Limited, Osaka, Japan

[21] Appl. No.: 615,751

[22] Filed: Sept. 22, 1975

[30] Foreign Application Priority Data

Sept. 20, 1974  Japan ............................ 49-108985
May 21, 1975  Japan ............................ 50-61233

[51] Int. Cl.² ........................................... C07C 103/52
[52] U.S. Cl. .............................. 260/112.5 R; 260/983;
544/21; 544/24; 544/26; 544/28; 544/29;
544/30; 544/16
[58] Field of Search ................... 260/112.5 R, 243 C, 260/983

[56] References Cited

U.S. PATENT DOCUMENTS 3,980,644  9/1976  Lunn ................................ 260/243 C 3,998,817  12/1976  Fukumura et al. ................ 260/243 C

OTHER PUBLICATIONS

Li et al., J. Am. Chem. Soc., 77, 1866–1870 (1955).

*Primary Examiner*—Delbert R. Phillips
*Attorney, Agent, or Firm*—Sughrue, Rothwell, Mion, Zinn and Macpeak

[57] ABSTRACT

An improved process for producing a peptide and a cephalosporin which comprises treating a phosphoramide derivative of the formula:

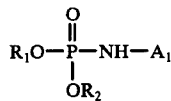

wherein $R_1$ and $R_2$ are each an alkyl group, a cycloalkyl group, an aryl group or an aralkyl group, and $A_1$ is a peptide residue or a cephalosporin residue, with a phosphorus acid to produce a peptide or a cephalosporin of the formula $A_1-NH_2$ wherein $A_1$ is as hereinbefore defined.

18 Claims, No Drawings

PREPARATION OF PEPTIDES AND CEPHALOSPORINS

BACKGROUND OF THE INVENTION

1. Field of the Invention

The present invention relates to an improved process for producing a peptide and a cephalosporin. More particularly, it relates to an improved process for elimination of a protective phosphoryl group in producing a peptide and a cephalosporin.

2. Description of the Prior Art

In general, in synthetic reactions of a compound containing a functional group, it is necessary to protect the functional group from taking part in the reaction depending on the object of the reaction, and then to remove the protective group selectively after the desired reaction is completed. Particularly, in the synthesis of the peptide of the formula (I) described herein, it is essential to protect the amino group and to remove the protective group.

An example in which the phosphoryl group of the formula

was used as a protective group for an amino group in the synthesis of a peptide, is disclosed in L. Zervas et al., Chem. Ber. 94, 2644 (1961). L. Zervas et al. used dibenzylphosphoryl or para-substituted dibenzylphosphoryl groups as a protective group for an amino group of an amino acid, and for the purpose of dephosphorylation employed the following two methods:

A. treatment of the N-phosphoryl peptide with hydrogen bromide in a solvent, and B. catalytic hydrogenation.

The method of treatment of the N-phosphoryl peptide with hydrogen bromide in a solvent, however, includes many problems, because of the high acidity of hydrogen bromide, in the preparation of a peptide which is unstable to acids. For example, a study recently made showed that, when this method was applied to the preparation of a peptide including a cephalosporin, it was difficult to avoid various side-reactions such as cleavage of the β-lactam ring in the cephalosporin nucleus. Therefore, this method is not suitable for this purpose.

On the other hand, the use of an expensive palladium catalyst is essential for the catalytic hydrogenation method, and moreover in the case of a peptide which contains a sulfur-containing amino acid such as cysteine and methionine as disclosed in, Helv. Chim. Acta., 42, 1257(1959), the catalyst is often easily poisoned and the catalytic hydrogenation ceases.

Furthermore, as described in Chem. Ber., 94, 2644 (1961) cited above, phosphoryl groups other than a dibenzylphosphoryl group or its para-substituted derivatives, for example, dialkylphosphoryl groups such as a diethylphosphoryl group, are not dephosphorylated by either of the methods (A) and (B) above. Dephosphorylation of N-phosphoryl groups contained in the above-mentioned peptides including a cephalosporin is disclosed in Dutch Pat. No. 7,200,432, and specifically 7-[5'-carboxy-5'-(diphenylphosphoramido)valeramido]-3-acetoxymethylceph-3-em-4-carboxylic acid is reacted with sodium acetate in methanol to obtain sodium 7-[5'-carboxy-5'-aminovaleramido]-3-acetoxymethyl-ceph-3-em-4-carboxylate. But, as the result of a study recently made, it has been found that this dephosphorylation method can not be employed for the dephosphorylation of all compounds of the formula (II) described herein.

SUMMARY OF THE INVENTION

One object of the present invention is to provide an advantageous process for preparing various peptides.

Another object of the present invention is to provide an industrially advantageous method for preparing a cephalosporin which is a very useful compound as an anti-microbial agent or a precursor thereof.

Further objects will be apparent from the following description.

These objects are achieved by a process for the elimination of a protective phosphoryl group of the formula (III):

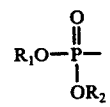

wherein $R_1$ and $R_2$ are each an alkyl group, a cycloalkyl group, an aryl group or an aralkyl group, from a phosphoramide derivative of the formula (II):

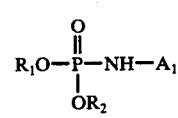

wherein $R_1$ and $R_2$ are as defined above and $A_1$ is a peptide residue or a cephalosporin residue to produce a peptide or a cephalosporin of the formula (I):

$$A_1-NH_2 \qquad (I)$$

wherein $A_1$ is as defined above by treating the phosphoramide derivative of the formula (II) with a phosphorus acid.

Thus, the invention provides a process for producing a peptide or a cephalosporin of the formula (I)

$$A_1-NH_2 \qquad (I)$$

wherein $A_1$ is a peptide residue or a cephalosporin residue derived from a peptide or cephalosporin, comprising treating a phosphoramide derivative of the formula (II):

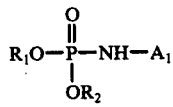

wherein $R_1$ and $R_2$ are each an alkyl group, a cycloalkyl group, an aryl group or an aralkyl group, with a phosphorus acid.

DETAILED DESCRIPTION OF THE INVENTION

In order to overcome the defects in conventional processes, various studies were conducted and it was found that a group represented by the formula (III):

$$R_1O-\overset{\overset{O}{\|}}{\underset{OR_2}{P}}- \quad \text{(III)}$$

wherein $R_1$ and $R_2$ are as defined hereinbefore, is stable during the course of synthesis of peptides and cephalosporins, and can be readily removed with a phosphorus acid under mild conditions, and therefore that the group can advantageously be used as a protective group during the synthesis of a peptide and a cephalosporin.

That is, as the dephosphorylation according to the present invention is carried out under a very mild condition, even an unstable peptide or cephalosporin, for example, the above-described ones including cephalosporins, can be dephosphorylated without side-reactions such as cleavage of the β-lactam ring of the cephalosporin nucleus occurring. Furthermore, in the present invention, the above-described phosphoryl group can be used in either case where the substituents, $R_1$ and $R_2$, are an alkyl group, a cycloalkyl group, an aryl group or an aralkyl group, and moreover can be used industrially advantageously because of the use of an inexpensive phosphorus acid.

In the above general formulas, $R_1$ and $R_2$ are each a $C_1$-$C_6$ alkyl group such as methyl, ethyl, isopropyl, n-butyl or n-amyl; a $C_3$-$C_7$ cycloalkyl group such as cyclohexyl or cyclopentyl; an aryl group such as phenyl, p-tolyl or p-chlorophenyl; and an aralkyl group such as benzyl, p-nitrobenzyl or p-chlorobenzyl; and the like.

The cephalosporin residue represented by $A_1$ in the formula (I) is a residue of a 7-amino-4-carboxy-3-cephem of the formula (I-a):

(I-a)

wherein $R_4$ is a formyl group, a hydroxy group, a lower alkyl group, a lower alkoxy group or a substituted methyl group and $R_3$ is a hydrogen atom, a lower alkyl group, a haloalkyl group, a lower alkoxy group, an aralkyl group, a hydroxy group, an aryloxy group, a lower alkanoyloxy group, a lower alkylsulfonyloxy group, a mercapto group, a lower alkylthio group, an arylthio group, an amino group, a lower alkylamino group, a lower alkanoylamino group, a lower alkanoyl group, a lower alkoxycarbonyl group, an aralkanoyl group, a carboxyl group, a formyl group, an azido group or a halogen atom, or the salt or the ester thereof.

Thus, the cephalosporin residue is a group of the formula (I-a'):

(I-a')

wherein $R_3$ and $R_4$ are as defined above. (With respect to the nomenclature for 3-cephem compound, reference is made to *Journal of the American Chemical Society*, 84, 3400 (1962).

As used herein, the term "lower alkyl group" includes a $C_1$-$C_4$ alkyl group such as methyl, ethyl, isopropyl, etc., the term "lower alkoxy group" means a $C_1$-$C_4$ alkoxy group such as methoxy, ethoxy, isopropoxy, etc., the term "substituted methyl group" means a methyl group substituted with a hydroxy group, a $C_1$-$C_4$ alkoxy group (e.g., methoxy, ethoxy, isopropoxy, etc.), a $C_2$-$C_5$ alkanoyloxy group (e.g., acetoxy), an aryloxy group (e.g., phenoxy), a carbamyloxy group, an amino group, a $C_1$-$C_4$ alkylamino group (e.g., methylamino), a $C_2$-$C_5$ alkanoylamino group (e.g., acetylamino), an azido group, a halogen atom or a group of the formula:

$$-S-R_5$$

wherein $R_5$ is a hydrogen atom or a $C_1$-$C_4$ alkyl group, an aryl group (e.g., phenyl) or a $C_2$-$C_5$ alkanoyl group (e.g., acetyl) or a heteroaromatic ring (e.g., pyridyl, 1,3,4-thiadiazol-2-yl, tetrazol-5-yl, etc.).

The term "haloalkyl group" means a $C_1$-$C_4$ alkyl group substitued with one or more halogen atoms such as 2-chloroethyl, 2,2,2-trichloroethyl, etc.

The term "aralkyl group" means a $C_1$-$C_4$ alkyl group substituted with an aryl group such as benzyl, etc.

An example of a "aryloxy group" is a phenoxy group.

The term "lower alkanoyloxy group" means a $C_2$-$C_5$ alkanoyloxy group such as acetoxy, etc.

The term "lower alkylsulfonyloxy group" means a $C_1$-$C_4$ alkylsulfonyloxy group such as methylsulfonyloxy, etc.

The term "lower alkythio group" includes a $C_1$-$C_4$ alkythio group such as methylthio, etc.

The term "arylthio group" preferably includes a phenylthio group.

The term "lower alkylamino group" means a $C_1$-$C_4$ alkylamino group such as methylamino, etc.

The term "lower alkanoylamino group" means a $C_2$-$C_5$ alkanoylamino group such as acetamido, etc.

The term "lower alkanoyl group" means a $C_2$-$C_5$ alkanoyl group such as acetyl, etc.

The term "lower alkoxycarbonyl group" means a $C_1$-$C_4$ alkoxycarbonyl group such as methoxycarbonyl, etc.

The term "aralkanoyl group" means a $C_1$-$C_4$ alkanoyl group substituted with an aryl group such as benzoyl.

The term "halogen atom" includes a chlorine, bromine, fluorine or iodine atom.

The carboxyl group at the 4-position may form a salt together with inorganic bases such as sodium hydroxide and potassium hydroxide, or together with organic bases such as triethylamine, quinoline and benzylamine; or may form an ester together with an ester protective group commonly employed in the synthesis of cephalosporin compounds.

Typical examples of such ester protective groups are alkyl groups such as a methyl group and a tert-butyl group, halogenated alkyl groups such as a 2,2,2-trichloroethyl group, aralkyl groups such as a benzyl group, a p-nitrobenzyl group, an o-nitrobenzyl group, a p-methoxybenzyl group, a 4-methoxy-3,5-di-tert-butylbenzyl group, a phenacyl group and a benzhydryl group, alkylsulfonylalkyl groups such as a methylsulfonylethyl group, trialkylsilyl groups such as a trimethylsilyl group, and the like. The ester protective groups and their function are well known in the art and can be freely selected by one skilled in the art so long as the function of protection is achieved.

The peptide represented also by the formula (I) designates a compound which includes at least two amino acids connected to each other through a peptide linkage. The peptide residue represented by the formula -$A_1$ in the formula (I) means a group formed by eliminating an amino group from the peptide of the formula (I).

The amino acids which make up the peptide can be any natural, synthetic and fermentation products, and further can be in any of an L-, D- and DL- forms. Specific examples of such amino acids include, for instance, glycine, alanine, valine, norvaline, leucine, isoleucine, serine, threonine, cysteine, cystine, methionine, sarcosine, aspartic acid, asparagine, glutamic acid, glutamine, lysine, ornithine, arginine, phenylalanine, tyrosine, histidine, tryptophan, proline, hydroxyproline, α-aminobutyric acid, γ-aminobutyric acid, α, γ-diaminobutyric acid, α-aminoadipic acid, α-phenylglycine, α-p-hydroxyphenylglycine, α-p-chlorophenylglycine, α-(2-thienyl)glycine, α-(2-furyl)glycine, α-(1-cyclohexenyl)glycine, and α-(1-cyclohexadienyl)glycine.

The term "amino acid" as used herein also includes the cephalosporin of the formula (I-a) as defined above.

The peptide represented by the formula (I) also includes a peptide in which other functional groups, if any, (e.g., amino, hydroxyl, carboxyl, mercapto, etc.) are protected with other conventional protective groups commonly employed in the art of the present invention.

The peptide and the cephalosporin represented by the formula (I), $A_1$—$NH_2$ are well-known substances useful as a medicine or a precursor thereof, and particularly, the cephalosporin is well-known as a potent antimicrobial agent or a precursor thereof.

The term "phosphorus acid" is employed herein to describe phosphorus acid type compounds such as ortho-phosphoric acid, phosphorous acid, phosphonic acid, phosphinic acid, and the ester and anhydride derivatives thereof. Specifically, suitable derivatives include phosphoric esters such as monomethyl phosphate, dimethyl phosphate, monoethyl phosphate, monophenyl phosphate, diphenyl phosphate and monobenzyl phosphate; phosphorous esters such as monomethyl phosphite and monophenyl phosphite; phosphoric acid anhydrides such as pyrophosphoric acid, polyphosphoric acid and phosphorus pentoxide; phosphoric ester anhydrides such as dimethyl pyrophosphate, diphenyl pyrophosphate and polyphosphoric ester; phosphonic acid derivatives such as methylphosphonic acid and phenylphosphonic acid; and phosphinic acid derivatives such as diethylphosphinic acid and diphenylphosphinic acid. Of these phosphorus acids, ortho-phosphoric acid, phosphorous acid, and polyphosphoric acid are particularly preferred industrially.

In carrying out the process of the present invention, the amount of phosphorus acid used in the reaction can vary from the phosphorus acid being present in excess to the compound of the formula (II) being present in excess, but an amount of more than 1 mole per mole of the compound of the formula (II), particularly, more than 3 moles is particularly preferred for obtaining good results. And since the phosphorus acid can act as the reaction medium, the amount of the phosphorus acid can range up to about 100 to 500 moles per mole of the compound of the formula (II).

According to the invention, the elimination of the phosphoryl group of the formula (III) is carried out by reacting the phosphoramide derivative of the formula (II) with a phosphorus acid in the absence of a solvent, or in a solution of suspension in an inert solvent.

When an inert solvent is employed, the amount of the inert solvent is such that the concentration of the phosphorus acid is more than about 10% by weight, but a concentration of 50 to 100% by weight (i.e., no solvent) is preferred particularly for obtaining good results.

Preferred examples of the inert solvents are as follows: aromatic hydrocarbons, e.g., benzene, toluene, etc.; chlorinated hydrocarbons, e.g., dichloromethane, chloroform, etc.; ethers, e.g., dioxane, diethyl ether, etc.; alcohols, e.g., methanol; amides such as dimethylformamide, etc.; dimethylsulfoxide; water; or carboxylic acids such as formic acid, acetic acid, propionic acid, etc.

The reaction suitably proceeds at temperatures above about −20° C, but in general, a temperature range between 0° C and 70° C is preferred for obtaining good results. Generally, the reaction is completed in a period of about 2 to 50 hours. Applying the process of the present invention, the peptide or cephalosporin of the formula (I) can be prepared in high yield by protecting the amino group in an amino acid, peptide or derivative thereof temporarily with the phosphoryl group of the formula (III), converting them to the desired peptides which still have this protective group, and then eliminating the amino protective group with a phosphorus acid under mild conditions.

Furthermore, as is well known in general, it is very important for isolation and purification of a compound containing functional group to protect the functional group temporarily, and in this respect the present invention is also very useful for achieving such a purpose. For example, in order to obtain a compound of the formula (I) in high purity, this purification can be achieved by converting the impure compound of the formula (I) to the phosphoryl derivative of the formula (II) by a well-known method, purifying the phosphoryl derivative of the formula (II), and then de-phosphorylating the derivative of the formula (II) to the compound of the formula (I) by the process of this invention.

The peptide of the formula (II) can be prepared by a conventional process per se in the art of the present invention, for instance, they can be prepared by reacting an amino acid or a peptide of the formula (IV):

$$A_2\text{—}NH_2 \qquad (IV)$$

which constitutes the peptide of the formula (I) together with an additional amino acid or peptide or which is the peptide of the formula (I), with a compound of the formula (V):

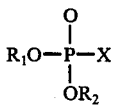

wherein $R_1$ and $R_2$ are each as defined above; and X is a halogen atom, to produce a compound of the formula (VI):

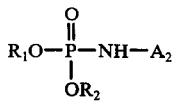

wherein $R_1$ and $R_2$ are each as defined above; and $A_2$ is the residual group of the amino acid or peptide of the formula (IV), and, if necessary, then expanding $A_2$ to $A_1$ by condensation of the compound of the formula (VI) with an additional amino acid or peptide.

The condensation can be carried out employing various condensation methods which are used in the art, for example, an acid halide method, a mixed acid anhydride method and a reactive ester method.

In the synthesis of the compounds represented by formulas (II) and (IV), it is of course necessary to previously protect functional groups which adversely affect the desired reaction with a suitable protective group as used in the art.

The compound of the formula (II) wherein $A_1$ is a cephalosporin residue is a novel compound where $R_4$ is other than a methyl group. The compound of the formula (II) wherein $A_1$ is a cephalosporin residue in which $R_3$ is a hydrogen atom and $R_4$ is a methyl group is disclosed in Swedish Patent Application No. 7315455-1 and German Patent Application (OLS) No. 2,357,097.

The following examples are given to illustrate the invention more specifically, but are not in any way to be construed as limiting the scope of the present invention. Unless otherwise indicated herein, all parts, percents, ratios and the like are by weight.

EXAMPLE 1

Preparation of 7-(D-α-Aminophenylacetamido)-3-methyl-ceph-3-em-4-carboxylic Acid Step A:

In 110 ml of an aqueous 1N-sodium hydroxide solution was dissolved 15 g of D-phenylglycine. To the resulting solution was added dropwise 20 g of dimethylphosphoryl chloride at room temperature (i.e., 20°-30° C) while keeping the pH of the reaction mixture at 9 to 11 with the addition of an aqueous 2N-sodium hydroxide solution.

The reaction mixture was stirred for an additional 20 minutes, washed with diethyl ether, adjusted to a pH of 2 with conc. hydrochloric acid and then extracted with dichloromethane. The organic layer was washed with water, dried over magnesium sulfate and concentrated to obtain 16 g of oily D-α-(dimethylphosphoramido)-phenylacetic acid.

$[\alpha]_D^{20}$ −152° (c = 0.5, CHCl$_3$)

IR: $\nu_{max}$ (neat) 1725 cm$^{-1}$

Three grams of the product thus-obtained was dissolved in 30 ml of dichloromethane and then 3 g of thionyl chloride was added thereto. The resulting solution was heated under reflux for 1 hour. The reaction solution was concentrated under reduced pressure to obtain 3.2 g of oily D-α-(dimethylphosphoramido)-phenylacetyl chloride. The product thus-obtained showed a strong absorption due to a carbonyl group (—COCl) at 1805 cm$^{-1}$ in the IR spectrum.

To a suspension of 2 g of 7-amino-3-methyl-ceph-3-em-4-carboxylic acid in 30 ml of water 2.4 g of sodium bicarbonate was added to dissolve the acid. The resulting solution was cooled to 0° to 5° C and a solution of 3 g of the acid chloride obtained above in 20 ml of acetone was added dropwise thereto while stirring. The reaction mixture was stirred for an additional 20 minutes, adjusted to a pH of 1 with addition of conc. hydrochloric acid and extracted with dichloromethane. The separated dichloromethane layer was dried over magnesium sulfate and concentrated. Diethyl ether was added to the residue and the precipitated crystals were filtered to obtain 2.3 g of 7-[D-α-(dimethylphosphoramido)phenylacetamido]-3-methyl-ceph-3-em-4-carboxylic acid (m.p. 190° - 192° C).

$[\alpha]_D^{20}$ +78° (c = 1, EtOH)

IR: $\nu_{max}$ (Nujol) 1780, 1715, 1660 cm$^{-1}$

Step B:

Two grams of 7-[D-α-(dimethylphosphoramido)-phenylacetamido]-3-methyl-ceph-3-em-4-carboxylic acid which was obtained in Step A above was dissolved in 5 ml of 85% phosphoric acid, and the resulting mixture was stirred at room temperature for 5 hours.

After 100 ml of diethyl ether was added to the reaction solution, the mixture was stirred vigorously for 5 minutes and allowed to stand. The ether layer was removed by decantation and the lower layer was washed again with diethyl ether by the same operation. Then, the washed layer was dissolved in 5 ml of water and the solution was adjusted to a pH of 4.3 with an aqueous 2N-sodium hydroxide solution. Then 15 ml of acetone was added thereto and the resulting mixture was allowed to stand overnight at 0° to 5° C. The precipitated crystals were filtered, washed with a small amount of water and acetone and dried under reduced pressure to obtain 1.2 g of 7-(D-α-aminophenylacetamido)-3-methyl-ceph-3-em-4-carboxylic acid as white crystals. The results of IR and TLC analysis of the product thus-obtained agreed completely those of an authentic sample.

$[\alpha]_D^{20}$ +151° (c = 0.5, H$_2$O)

EXAMPLE 2

Preparation of 2,2,2-Trichloroethyl 7-(D-α-Aminophenylacetamido)-3-methyl-ceph-3-em-4-carboxylate Step A:

In 10 ml of dichloromethane were dissolved 1.36 g of D-α-(dimethylphosphoramido)phenylacetic acid and 0.41 g of N-methyl morpholine and the resulting mixture was cooled to −15° to −10° C. To the mixture was added 0.43 g of ethyl chlorocarbonate and, after stirring the mixture for 10 minutes at the same temperature, 1.53 g of 2,2,2-trichloroethyl 7-amino-3-methylceph-3-em-4-carboxylate hydrochloride was added thereto. Thereafter, additional N-methyl morpholine (0.41 g) was added dropwise over a 15 minute period. After stirring the reaction solution for 1 hour at the same temperature, the solution was washed successively with 1N-hydrochloric acid and a saturated aqueous sodium bicarbonate solution, dried over magnesium sulfate and concentrated. The residue was recrystallized from a mixed solvent of isopropyl alcohol and n-hexane to obtain 1.89 g of 2,2,2-trichloroethyl 7-[D-α-(dimethylphosphoramido)phenylacetamido]-3-methyl-ceph-3-em-4-carboxylate (m.p. 99° ~ 102° C).

IR: $\nu_{max}$(Nujol) 1780, 1740, 1680 cm$^{-1}$

Step B:

In 5 g of 85% phosphoric acid was dissolved 1.5 g of 2,2,2-trichloroethyl 7-[D-α-(dimethylphosphoramido)-phenylacetamido]-3-methyl-ceph-3-em-4-carboxylate which was obtained in Step A above, and the resulting mixture was stirred for 10 hours at room temperature. After adding 30 ml of water to the reaction mixture, the mixture was adjusted to a pH of 6 with a 2N aqueous sodium hydroxide and extracted with ethyl acetate. The ethyl acetate layer was washed with water, dried over magnesium sulfate and concentrated to obtain 1.16 g of 2,2,2-trichloroethyl 7-(D-α-aminophenylacetamido)-3-methyl-ceph-3-em-4-carboxylate as a pale yellow solid.

IR: $\nu_{max}$(CHCl$_3$) 1780, 1740, 1685 cm$^{-1}$

NMR (CDCl$_3$) δ:
1.96 (2H, singlet, NH$_2$),
2.21 (3H, singlet, 3-CH$_3$),
3.40 (2H, multiplet, —S—CH$_2$—),
5.78 (1H, multiplet, 7-H),
7.36 (5H, singlet, aromatic ring),
7.96 (1H, doublet, J=10Hz, —CONH—).

EXAMPLE 3

Preparation of Phenacyl 7-(D-α-Aminophenylacetamido)-3-methyl-ceph-3-em-4-carboxylate Hydrochloride Step A:

To 110 ml of a 1N aqueous sodium hydroxide solution was added 15 g of D-phenylglycine. To the mixture was added dropwise 20 g of diisopropylphosphoryl chloride at room temperature, while keeping the pH of the reaction mixture of 9 to 11 by the addition of a 2N aqueous sodium hydroxide solution.

The reaction mixture was stirred for an additional 20 minutes, cooled to 0° to 5° C, and then adjusted to a pH of 2 with conc. hydrochloric acid. After the reaction solution was stirred for 30 minutes at the same temperature, the precipitated crystals were filtered and dried over phosphorus pentoxide under reduced pressure to obtain 30 g of D-α-(diisopropylphosphoramido)-phenylactic acid (m.p. 124° - 126° C).

[α]$_D^{20}$ −144° (c = 1, CHCl$_3$)

In 30 ml of dichloromethane were dissolved 3.15 g of the carboxylic acid thus-obtained above and 1.04 g of triethylamine, and to the resulting solution 1.12 g of ethyl chlorocarbonate was added dropwise at −15° to −10° C while stirring. The reaction mixture was stirred at the same temperature for an additional 10 minutes. Then, 3.69 g of phenacyl 7-amino-3-methyl-ceph-3-em-4-carboxylate hydrochloride was added thereto and subsequently 1.01 g of triethylamine was added dropwise thereto over a 15 minute period. After the mixture was stirred at the same temperature for an additional hour, the reaction mixture was washed successively with 1N-hydrochloric acid and a saturated aqueous sodium bicarbonate solution, dried over magnesium sulfate and concentrated. The residue was recrystallized from a mixed solvent of dichloromethane and ethyl acetate to obtain 5.86 g of phenacyl 7-[D-α-(diisopropylphosphoramido)phenylacetamido]-3-methyl-ceph-3-em-4-carboxylate (m.p. 224° ~ 225° C).

IR: $\nu_{max}$(Nujol) 1785, 1740, 1685, 1660 cm$^{-1}$

Step B:

In 10 ml of polyphosphoric acid was dissolved 3 g of phenacyl 7-[D-α-(diisopropylphosphoramido)-phenylacetamido]-3-methyl-ceph-3-em-4-carboxylate, and the resulting mixture was stirred at room temperature for 10 hours. After adding 50 ml of water to the reaction mixture, the mixture was adjusted to a pH of 6 by the addition of a 2N aqueous sodium hydroxide solution and then extracted with dichloromethane. The dichloromethane layer was cooled to 0° to 5° C and then 5 ml of a 3N-hydrochloric acid was added thereto while stirring. After the solution was stirred for 3 hours at the same temperature, the precipitated crystals were filtered to obtain 2.2 g of phenacyl 7-(D-α-aminophenylacetamido)-3-methyl-ceph-3-em-4-carboxylate hydrochloride (m.p. 178° ~ 180° C.).

IR: $\nu_{max}$(Nujol) 1762, 1718, 1690, 1670 cm$^{-1}$

EXAMPLE 4

Preparation of 7-(D-α-Aminophenylacetamido)-3-methyl-ceph-3-em-4-carboxylic Acid Step A:

In 30 ml of formic acid was dissolved 3 g of phenacyl 7-[D-α-(diisopropylphosphoramido)phenylacetamido]-3-methyl-ceph-3-em-4-carboxylate. To the resulting mixture was added 1.5 g of zinc powder, and the mixture was stirred at 5° to 10° C for 2 hours.

After completion of the reaction, the excess zinc powder was filtered off and the filtrate was concentrated under reduced pressure. To the resulting residue was added 30 ml of 1N-hydrochloric acid and the mixture was extracted with dichloromethane. The organic layer was washed with water, dried over magnesium sulfate and concentrated. Diethyl ether was added to the residue, and the precipitated crystals were filtered to obtain 2.1 g of 7-[D-α-(diisopropylphosphoramido)-phenylacetamido]-3-methyl-ceph-3-em-4-carboxylic acid (m.p. 146° ~ 147° C).

[α]$_D^{25}$ +53° (c = 1, EtOH)

IR: $\nu_{max}$(Nujol) 1790, 1720, 1665 cm$^{-1}$

Step B:

In 5 ml of 85% phosphoric acid was dissolved 2 g of 7-[D-α-(diisopropylphosphoramido)phenylacetamido]-3-methyl-ceph-3-em-4-carboxylic acid, and the resulting mixture was stirred at room temperature for 8 hours. The solution was treated in the same manner as described in Example 1 to obtain 1.0 g of 7-(D-α-aminophenylacetamido)-3-methyl-ceph-3-em-4-carboxylic acid. The IR spectrum of the product thus-obtained agreed completely with that of an authentic sample.

$[\alpha]_D^{20} +148°$ (c = 0.5, H$_2$O)

EXAMPLE 5

Preparation of L-Alanyl-L-leucine Methyl Ester Hydrochloride

In 10 g of polyphosphoric acid dissolved 3 g of N-[bis-(p-nitrobenzyl)phosphoryl]-L-alanyl-L-leucine methyl ester (which was prepared as disclosed in Chem. Ber., 94, 2644 (1961)), and the reaction mixture was allowed to stand at room temperature for 18 hours.

After the reaction was completed, 30 ml of water was added. The precipitated crystals (which were identified with bis-(p-nitrobenzyl)phosphate on the basis of elemental analysis and the IR spectrum and the melting point were in complete agreement those of an authentic sample) were filtered, and the filtrate was neutralized with solid sodium bicarbonate and extracted with ethyl acetate. To the separated ethyl acetate layer was added 1 ml of conc. hydrochloric acid, and the mixture was concentrated to half of the original volume. The precipitated crystals were filtered to obtain 1.2 g of L-alanyl-L-leucine methyl ester hydrochloride.

$[\alpha]_D^{20} +5.5°$ (c = 1, methanol)

m.p. 178° ~ 179° C

EXAMPLE 6

Preparation of S-Benzyl-L-cysteinylglycine

Step A:

In 80 ml of 0.1N aqueous sodium hydroxide was dissolved 6.3 g of S-benzyl-L-cysteine, and 5.7 g of dimethylchlorophosphate was added dropwise at 25° to 30° C over a 30 minute period followed by stirring at the same temperature for 30 minutes. The reaction mixture was washed with diethyl ether, acidified with a 6N aqueous hydrochloric acid solution to a pH of 2 and extracted with dichloromethane. The dichloromethane layer was washed with water, dried over anhydrous magnesium sulfate and concentrated under reduced pressure to obtain 6.7 g of S-benzyl-N-dimethylphosphoryl-L-cysteine as a colorless oil.

IR: $\nu_{max}$ (film) 1735 cm$^{-1}$ $[\alpha]_D^{25} +28°$ (c = 1, CHCl$_3$)

To a mixture of 50 ml of dichloromethane, 6.4 g of the product thus-obtained, 2.8 g of glycine ethyl ester hydrochloride and 4.1 g of triethylamine was added 4.5 g of dicyclohexylcarbodiimide. The mixture was allowed to stand at room temperature for 20 hours. After the precipitate was removed by filtration, the reaction mixture was washed successively with a 1N aqueous hydrochloric acid solution and a 5% aqueous potassium bicarbonate solution, dried over anhydrous magnesium sulfate and concentrated under reduced pressure to obtain 7.3 g of (S-benzyl-N-dimethylphosphoryl)-L-cysteinylglycine ethyl ester as an oil.

IR: $\nu_{max}$ (film) 1740, 1655 cm$^{-1}$

The product thus-obtained was used for the next step without further purification.

Step B:

In 30 g of 85% phosphoric acid was dissolved 6.1 g of the product obtained in Step A above, and the mixture was stirred at room temperature for 20 hours. After 100 ml of water was added, the reaction mixture was adjusted to a pH of 7 with a 30% aqueous sodium hydroxide solution and extracted with ethyl acetate. The separated ethyl acetate layer was dried over anhydrous magnesium sulfate and concentrated under reduced pressure to obtain 4.5 g of S-benzyl-L-cysteinylglycine ethyl ester as an oil.

IR: $\nu_{max}$ (film) 1740, 1650 cm$^{-1}$

Saponification of the product thus-obtained by treatment with a methanolic sodium hydroxide solution produced 3.8 g of S-benzyl-L-cysteinylglycine.

m.p. 163° – 164° C $[\alpha]_D^{25} +28°$ (c = 1, 1N NaOH)

While the invention has been described in detail and with reference to specific embodiments thereof, it will be apparent to one skilled in the art that various changes and modifications can be made therein without departing from the spirit and scope thereof.

What is claimed is:

1. A process for preparing a cephalosporin of the formula:

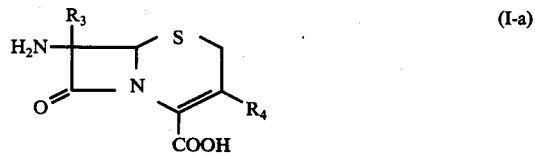

wherein R$_4$ is formyl, hydroxyl, C$_1$–C$_4$ alkyl, C$_1$–C$_4$ alkoxy or a methyl group substituted with hydroxy, C$_1$–C$_4$ alkoxy, C$_2$–C$_5$ alkanoyloxy, phenoxy, carbamyloxy, C$_1$–C$_4$ alkylamino, C$_2$–C$_5$ alkanoylamino, azido, halogen, or a group of the formula:

—S—R$_5$ wherein R$_5$ is hydrogen, C$_1$–C$_4$ alkyl, phenyl, C$_2$–C$_5$ alkanoyl, pyridyl, 1,3,4-thiadiazol-2-yl, or tetrazol-5-yl; and R$_3$ is hydrogen, C$_1$–C$_4$ alkyl, C$_1$–C$_4$ haloalkyl, C$_1$–C$_4$ alkoxy, phenyl(C$_1$–C$_4$)alkyl, hydroxy, phenoxy, C$_2$–C$_5$ alkanoyloxy, C$_1$–C$_4$ alkylsulfonyloxy, mercapto, C$_1$–C$_4$ alkylthio, phenylthio, amino, C$_1$–C$_4$ alkylamino, C$_2$–C$_5$ alkoxycarbonyl, phenyl(C$_2$–C$_5$)alkanoyl, carboxyl, formyl, azido, or halogen, or the salt or the ester thereof, which comprises reacting a phosphoramide derivative of the formula:

wherein R$_1$ and R$_2$ are each C$_1$–C$_6$ alkyl, C$_3$–C$_7$ cycloalkyl, phenyl, p-tolyl, p-chlorophenyl, benzyl, p-nitrobenzyl, or p-chlorobenzyl; and A$_1$ is a cephalosporin residue of the formula:

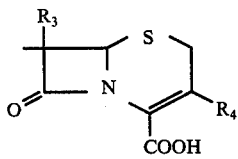

(I-a')

wherein R₃ and R₄ are as defined above, with a phosphorus acid, or the ester or the anhydride thereof.

2. The process according to claim 1, wherein said phosphorus acid is ortho-phosphoric acid; phosphorous acid; phosphonic acid; phosphinic acid; and the esters and anhydrides thereof.

3. The process according to claim 2, wherein said phosphoric ester is monomethyl phosphate, dimethyl phosphate, monoethyl phosphate, monophenyl phosphate, diphenyl phosphate or monobenzyl phosphate; said phosporous ester is monoethyl phosphite or monophenyl phosphite; said phosphoric acid anhydride is pyrophosphoric acid, polyphosphoric acid or phosphorus pentoxide; said phosphoric ester anhydride is dimethyl pyrophosphate, diphenyl pyrophosphate or polyphosphoric ester; said phosphonic acid is methylphosphonic acid or phenylphosphonic acid; and said phosphinic acid is dimethylphosphinic acid or diphenylphosphinic acid.

4. The process according to claim 2, wherein said phosphorus acid is ortho-phosphoric acid, phosphorous acid or polyphosphoric acid.

5. The process according to claim 1, wherein the reacting is at about 0° to 70° C.

6. The process according to claim 1, wherein the reaction is in a mixture of said derivative of the formula (II) and said phosphorus acid or in a solution or suspension in an inert solvent of said derivative of the formula (II) and said phosphorus acid.

7. The process according to claim 6, wherein said inert solvent is an aromatic hydrocarbon, an aliphatic chlorinated hydrocarbon, an ether, an alcohol, an amide, water, or a carboxylic acid.

8. The process according to claim 7, wherein said inert solvent is benzene, toluene, dichloromethane, chloroform, dioxane, diethyl ether, methanol, dimethylformamide, water or acetic acid.

9. The process according to claim 1, wherein the amount of said phosphorus acid is greater than 1 mole of said phosphorus acid per mole of the derivative of the formula (II).

10. A process for producing a peptide derivative made from at least two amino acid compounds selected from the group consisting of glycine, alanine, valine, norvaline, leucine, isoleucine, serine, theronine, cysteine, cystine, methionine, sarcosine, aspartic acid, asparagine, glutamic acid, glutamine, lysine, ornithine, arginine, phenylalanine, tyrosine, hitidine, triptophan, proline, hydroxyproline, α-aminobutyric acid, γ-aminobutyric acid, γ,α-diaminobutyric acid, α-aminoadipic acid, αphenyglycine, α-p-hydroxyphenylglycine, α-p-chlorophenylglycine, α-(2-thienyl)-glycine, α-(2-furyl)glycine, α-(1-cyclohexenyl)glycine, α-(1-cyclohexadienyl)glycine, and their protected derivative and a cephalosporin of the formula:

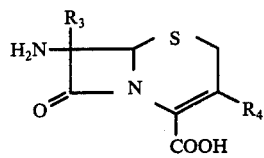

(I-a)

wherein R₄ is formyl, hydroxy, $C_1$-$C_4$ alkyl, $C_1$-$C_4$ alkoxy or a methyl group substituted with hydroxy, $C_1$-$C_4$ alkoxy, $C_2$-$C_5$ alkanoyloxy, phenoxy, carbamyloxy, amino, $C_1$-$C_4$ alkylamino, $C_2$-$C_5$ alkanoylamino, azido, halogen, or a group of the formula:

$$-S-R_5$$

wherein $R_5$ is hydrogen, $C_1$-$C_4$ alkyl, phenyl, $C_2$-$C_5$ alkanoyl, pyridyl, 1,3,4thiadiazol-2-yl, or tetrazol-5-yl; and $R_3$ is hydrogen, $C_1$-$C_4$ alkyl, $C_1$-$C_4$ haloalkyl, $C_1$-$C_4$ alkoxy, phenyl($C_1$-$C_4$)alkyl, hydroxy, phenoxy, $C_2$-$C_5$ alkanoyloxy, $C_1$-$C_4$ alkylsulfonyloxy, mercapto, $C_1$-$C_4$ alkylthio, phenylthio, amino, $C_1$-$C_4$ alkylamino, $C_2$-$C_5$ alkoxycarbonyl, phenyl($C_2$-$C_5$)alkanoyl, carboxyl, formyl, axido, or halogen, or the salt or the ester thereof, which comprises reacting a phosphoramide derivative of the formula:

(II-b)

wherein $R_1$ and $R_2$ are each $C_1$-$C_6$ alkyl, $C_3$-$C_7$ cycloalkyl, phenyl, p-toyl, p-chlorophenyl, benzyl, p-nitrobenzyl, or p-chlorobenzyl, the amino group (—NH—) is a terminal or free amino group of said peptide derivative and $A_{11}$ is the residual part of the peptide derivative, with a phosphorus acid, or the ester or the anhydride thereof.

11. The process according to claim 10, wherein said phosphorus acid is ortho-phosphoric acid; phosphorous acid; phosphonic acid; phosphinic acid; and the esters and anhydrides thereof.

12. The process according to claim 11, wherein said phosphoric ester is monomethyl phosphate, dimethyl phosphate, monoethyl phosphate, monophenyl phosphate, diphenyl phosphate or monobenzyl phosphate, said phosphorous ester is monoethyl phosphite or monophenyl phosphite; said phosporic acid anhydride is pyrophosphoric acid, polyphosphoric acid or phosphorus pentoxide; said phosphoric ester anhydride is dimethyl pyrophosphate, diphenyl pyrophosphate or polyphosphoric ester; said phosphonic acid is methylphosphonic acid or phenylphosphonic acid; and said phosphinic acid is dimethylphosphinic acid or diphenylphosphinic acid.

13. The process according to claim 11, wherein said phosphorus acid is ortho-phosphoric acid, phosphorous acid or polyphosphoric acid.

14. The process according to claim 10, wherein the reacting is at about 0° to 70° C.

15. The process according to claim 10, wherein the reacting is in a mixture of said derivative of the formula (II) and said phosphorus acid or in a solution or suspension in an inert solvent of said derivative of the formula (II) and said phosphorus acid.

16. The process according to claim 15, wherein said inert solvent is an aromatic hydrocarbon, an aliphatic chlorinated hydrocarbon, an ether, an alcohol, an amide, water, or a carboxylic acid.

17. The process according to claim 16, wherein said inert solvent is benzene, toluene, dichloromethane, chloroform, dioxane, diethyl ether, methanol, dimethylformamide, water or acetic acid.

18. The process according to claim 10, wherein the amount of said phosphorus acid is greater than 1 mole of said phosphorus acid per mole of the derivative of the formula (II).

* * * * *